(12) United States Patent
Yanagawa et al.

(10) Patent No.: US 7,041,446 B2
(45) Date of Patent: May 9, 2006

(54) LABELED PROTEIN AND ITS PRODUCING METHOD, LABELING COMPOUND TO BE USED IN THE METHOD, AND METHOD FOR ANALYZING FUNCTION OF GENES

(75) Inventors: Hiroshi Yanagawa, Machida (JP); Naoto Nemoto, Machida (JP); Etsuko Miyamoto, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 130 days.

(21) Appl. No.: 09/794,128

(22) Filed: Feb. 28, 2001

(65) Prior Publication Data

US 2001/0007751 A1    Jul. 12, 2001

Related U.S. Application Data

(62) Division of application No. 09/190,276, filed on Nov. 13, 1998, now Pat. No. 6,228,994.

(30) Foreign Application Priority Data

May 15, 1998   (JP) .................................. 10-133170

(51) Int. Cl.
*C12Q 1/68* (2006.01)
*C07K 1/13* (2006.01)

(52) U.S. Cl. .......................................... 435/6; 530/402

(58) Field of Classification Search .................... 435/6; 530/402
See application file for complete search history.

(56) References Cited

U.S. PATENT DOCUMENTS 6,281,344 B1 *  8/2001  Szostak et al. ............. 536/23.1
6,660,473 B1   12/2003  Lohse et al. ................... 435/6

FOREIGN PATENT DOCUMENTS

EP    0 962 527    12/1999
WO    98/16636    4/1998

OTHER PUBLICATIONS

"Program and Proceedings of the 20th Annual Meeting of the Molecular Biology Society of Japan", Nov. 15, 1997, pp. 121, 546 and 547, together with a summarized translation.
*Progress in Biophysics and Molecular Biology*, XIIth International Biophysics Congress, abstract No. P-A5-04 (Aug. 1996).
Promega Technical Bulletin, No. 182 (Sep. 1993).
N. Nemoto et al., *FEBS Letters*, 414, 405-408 (1997).
R. Vince et al., "Photoaffinity Labeling of the Ribosomal Peptidyl Transferase Site with Synthetic Puromycin Analogues", Biochemistry, vol. 17, No. 25, pp. 5489-5493, 1978.

* cited by examiner

*Primary Examiner*—Rebecca Prouty
(74) *Attorney, Agent, or Firm*—Wenderoth, Lind & Ponack, L.L.P.

(57) ABSTRACT

A protein having a labeling compound attached to its C-terminal, in which the compound comprises a label portion comprising a label substance and an acceptor portion comprising a compound having an ability of binding to a C-terminal of a synthesized protein when protein synthesis is carried out in a cell-free protein synthesis system or in a living cell is provided. Also, a method for producing the protein comprising the step of performing synthesis of a protein in a cell-free protein synthesis system or in a living cell in the presence of a labeling compound comprising a label portion comprising a label substance and an acceptor portion comprising a compound having an ability of binding to a C-terminal of a synthesized protein when protein synthesis is carried out in the cell-free protein synthesis system or in the living cell, the labeling compound being present at a concentration effective for the labeling compound to bind to the C-terminal of the synthesized protein is provided. Also, the labeling compound and a method for analyzing a function of a gene are further provided.

7 Claims, 4 Drawing Sheets

LABELED PROTEIN AND ITS PRODUCING METHOD, LABELING COMPOUND TO BE USED IN THE METHOD, AND METHOD FOR ANALYZING FUNCTION OF GENES

This application is a divisional of Ser. No. 09/190,276, filed Nov. 13, 1998, now U.S. Pat. No. 6,228,994.

BACKGROUND OF THE INVENTION

The present invention relates to a labeled protein and its producing method and a labeling compound to be used in the method. Also the present invention relates to a method for analyzing function of genes.

For labeling of protein expressed in cell-free translation systems and living cells is used generally a radiolabeling method that involves incorporating an amino acid labeled with a radioactive element such as $^{35}S$, $^{3}H$, $^{14}C$ or the like into the translation product. However, amino acids may be used in reactions other than protein synthesis so that it happens that substances other than the translation product may be also labeled. On the other hand, the labeling method specific to the translation product includes the following method. To the ε-amino group of lysine, biotin is covalently linked, and the product is further linked through an ester linkage to tRNA having an anticodon for lysine to synthesize a complex (biotin-lysine-tRNA), which is put into a cell-free translation system to biotinate the translation product. The translation product is electrophoresed and then transferred on a membrane, and allowed to chemiluminesce with an alkali phosphatase by using a fusion protein of the alkaline phosphatase and streptoavidine. This chemiluminescence is recorded using X-ray film or the like for identifying the translation product (Promega, (1993) Technical Bulletin, No. 182, p.2). However, this method suffers from extreme instability of the synthesized biotin-lysine-tRNA (for 6 months at −70° C.) and is expensive. Further, there is the problem that the procedure for identification is complicated and time-consuming. This is disadvantageous in automation for processing on a large scale. The translated protein is modified by biotin at a plurality of lysine side chains so that there is the possibility that its function and structure vary from the original one.

SUMMARY OF THE INVENTION

It is an object of the present invention to provide a methodology which satisfies conditions such as 1) simplicity, 2) economically competitiveness, 3) long-term stability, and 4) no adverse influence on the function and structure of the translation product in labeling of translated protein in a cell-free translation system and living cells.

As a result of intensive investigation with view to overcoming the above-described problems, it has now been found that puromycin or its derivatives binds or bind to the C-terminal of a translated protein in a final concentration of 10 to 0.01 μM. It has also been found that the compound obtained by chemically linking a fluorescent substance such as fluorescein to puromycin binds to the C-terminal of the translated protein like puromycin and use of this enables one to identify proteins. That is, by adding the fluorescent puromycin to a cell-free translation system to carry out reaction, and then subjecting the product to gel electrophoresis, the gel without further processing can be read by a fluorescent image analyzer to identify the translated protein without difficulty. The present invention has been completed based on these findings.

Thus the present invention provides a labeling compound for labeling a protein, which comprises a label portion comprising a label substance and an acceptor portion comprising a compound having an ability of binding to a C-terminal of a synthesized protein when protein synthesis is carried out in a cell-free protein synthesis system or in a living cell, and a protein having the labeling compound attached to its C-terminal.

According to another aspect of the present invention, there is provided a method for producing the protein comprising the step of carrying out synthesis of a protein in a cell-free protein synthesis system or in a living cell in the presence of a labeling compound comprising a label portion comprising a label substance and an acceptor portion comprising a compound having an ability of binding to a C-terminal of a synthesized protein when protein synthesis is carried out in the cell-free protein synthesis system or in the living cell, the labeling compound being present at a concentration effective for the labeling compound to bind to the C-terminal of the synthesized protein.

Further, according to another aspect of the present invention, there is provided a method for analyzing a function of a gene, comprising the steps of: adding a nucleic acid containing the gene to a cell-free protein synthesis system as a template; carrying out protein synthesis in the presence of a labeling compound to obtain a protein having the labeling compound attached to the C-terminal of the protein, the labeling compound being present at a concentration effective for the labeling compound to bind to the C-terminal of the synthesized protein; and analyzing a function of the labeled protein.

The label portion preferably comprises a radioactive substance or a non-radioactive label substance.

The acceptor portion preferably comprises a nucleic acid derivative. Alternatively, the acceptor portion preferably comprises a compound comprising a nucleic acid and an amino acid or an amino acid derivative which are bound to each other. More preferably, the acceptor portion comprises a compound comprising 2'- or 3'-aminoadenosine or its derivative and an amino acid or an amino acid derivative which are bound to each other. Particularly preferably, the acceptor portion comprises puromycin or its derivative.

The analysis of the function of protein preferably comprises determination of a protein-protein interaction, determination of a protein-nucleic acid interaction, or determination of an interaction between a protein and a ligand capable of specifically binding to the protein.

The labeling compound of the present invention is useful in detection and identification of a protein that is expressed in various cell-free protein synthesis systems or in living cells. In the future, the identification of corresponding proteins is most important theme in the functional analysis of genes that accumulate by genome analysis. The present invention provides effective means for increasing the efficiency of or automating analysis of function of protein such as a protein-nucleic acid interaction or a protein-protein interaction.

BRIEF EXPLANATION OF THE DRAWINGS

FIG. 4B is a photograph of an electrophoretogram illustrating the influence of Fluorthiopur (FluorS-Pur) concentration. The arrow indicates the position of apparent molecular weight of 12 kDa in the full-length protein of thioredoxin. FIG. 4C is a photograph electrophoretogram corresponding to the gel stained with CBB which is a dye usually used for staining proteins, after detecting the gel of the upper electrophoretogram by fluorimetry. The leftmost lane in the lower electrophoretogram corresponds to a supernatant of disrupted cells that were obtained by incubating *E. coli* strain BL21(DE3) harboring a plasmid (pT-Trx) containing T7 promoter and a coding region for coding *E. coli* thioredoxin (135 amino acid residues, molecular weight: 14 kDa, apparent molecular weight: 12 kDa) in LB medium in the presence of chloramphenicol (final concentration: 34 μg/ml) at 37° C., and causing mass expression of thioredoxin by addition of IPTG. This indicates mass expression of thioredoxin at the position of apparent molecular weight of 12 kDa.

DETAILED DESCRIPTION OF THE INVENTION

Figure 1:
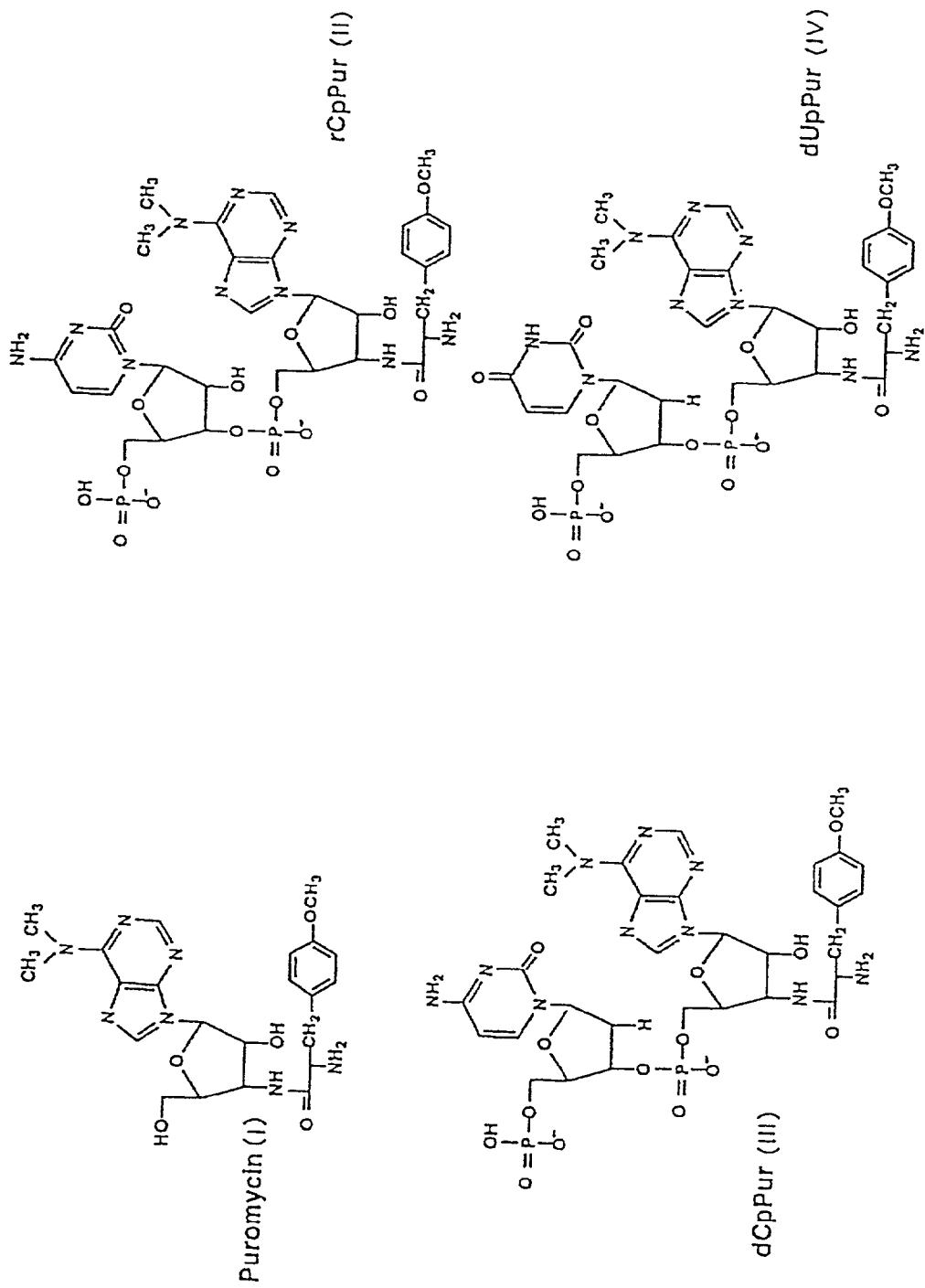
FIG. 1 shows the chemical structure of puromycin and its derivatives. I is puromycin, II is rCpPur, III is dCpPur, and IV is dUpPur.

The labeling compound of the present invention comprises a "label portion" that comprises a label substance and an "acceptor portion" that comprises a compound having an ability of binding to the C-terminal of a protein. The label and acceptor portions are linked through a chemical bond. The label portion and acceptor portion may be chemically bound either directly or thorough a linker.

The label substance may be either a radioactive substance or a non-radioactive label substance. The radioactive substance includes $^{33}$P, $^{32}$P, $^{35}$S and the like. The non-radioactive label substance includes fluorescent substances, coenzymes such as biotin, proteins, peptides, sugars, lipids, dyes, polyethylene glycol, and the like. The kind and size of the compounds are not limited unless the binding of the labeling compound to the C-terminal of protein is prevented.

The fluorescent substance may be any type of fluorescent dye as far as it has a free functional group (for example, a carboxyl group, a hydroxyl group, an amino group, etc.) and can be bound to the acceptor portion through a linker (for example, fluorescein series, rhodamine series, eosin series, NBD series, etc.). Preferably, the fluorescent substance is one belonging to the fluorescein series.

The label substance is preferably, from the viewpoint that a measuring apparatus is commercially spread, a radioactive substance or a fluorescent substance.

The acceptor portion may be any compound as far as the compound has an ability of binding to the C-terminal of a synthesized protein when synthesis (translation) of the protein is carried out in a cell-free protein synthesis system or in a living cell. Usually, the acceptor portion is a compound in which a compound containing a chemical structure skeleton that resembles a nucleic acid or its repeated structure and an amino acid or a compound having a chemical structure skeleton that resembles an amino acid are chemically bound to each other (nucleic acid derivative). There can be utilized those having an amido linkage as the chemical bond such as puromycin, and 3'-N-aminoacylpuromycin aminonucleoside (PANS-amino acid), for example, PANS-Gly, which contains glycine as the amino acid moiety, PANS-Val, which contains valine as the amino acid moiety, PANS-Ala, which contains alanine as the amino acid moiety, and the like and all the other PANS-amino acids corresponding to all the amino acids. 3'-N-Aminoacyladenosine aminonucleoside (AANS-amino acid) having as the chemical bond an amido linkage formed by condensation with dehydration between the amino group of 3'-aminoadenosine and a carboxyl group of an amino acid, for example, AANS-Gly, which contains glycine as the amino acid moiety, AANS-Val, which contains valine as the amino acid moiety, AANS-Ala, which contains alanine as the amino acid moiety, and the like and all the other AANS-amino acids corresponding to all the amino acids. Also, there can be used those compounds in which a nucleoside or nucleotide and an amino acid are bound through an ester linkage. In addition, there can be utilized all the compounds that contain a linkage of any type allowing a compound having a chemical structure skeleton that resembles a nucleic acid and an amino acid or a compound having a chemical structure skeleton that resembles an amino acid to chemically bind to each other.

The term "nucleic acid" used herein means a nucleoside or its derivatives, or a repeated structure linked through a diester linkage with intervening phosphate between 3'-carbon and 5'-carbon.

The acceptor portion comprises preferably a compound that comprises a nucleic acid and an amino acid or its derivative which are linked to each other. More preferably, the acceptor portion comprises a compound that comprises 2'- or 3'-aminoadenosine or its derivative and an amino acid or its derivative which are linked to each other. Particularly preferred are puromycin and its derivatives.

Specific examples of the acceptor portion include ribocytidyl puromycin (rCpPur, Compound II in FIG. 1), deoxycytidyl puromycin (dCpPur, Compound III in FIG. 1), and deoxyuridyl puromycin (dUpPur, Compound IV in FIG. 1).

The ability of the compound which constitutes the acceptor portion to bind to the C-terminal of a protein when the synthesis (translation) of the protein is carried out in a cell-free protein synthesis system or in a living cell can be evaluated by carrying out the synthesis of a protein in the cell-free protein synthesis system or in the living cell in the presence of that compound and measuring the production of a peptidyl compound.

The cell-free protein synthesis system or the living cell is not limited to particular one as far as protein synthesis can proceed when a nucleic acid encoding the protein is added or introduced therein. As the cell-free protein synthesis system, there can be used a cell-free protein synthesis system of procaryote or eucaryote, for example, cell-free protein synthesis systems of *E. coli*, rabbit reticulocyte, wheat germ and the like. As the protein synthesis system may be used either a cell-free transcription-translation system or a cell-free translation system depending on whether the nucleic acid used as a template is DNA or RNA. As the living cell, there may be used a cell of procaryotes such as *E. coli* or eucaryotes.

The labeling compound can be produced by linking the label portion and the acceptor portion by a known chemical linking method.

As an example in which the label portion comprises a radioactive substance, first puromycin and rC-β-amidite are coupled and then the protective group is removed to synthesize rCpPur. In a similar manner, dCpPur and dUpPur can be synthesized. Then these compounds may be phosphorylated by T4 polynucleotide kinase in the presence of γ-$^{33}$P-ATP to prepare a labeling compound of which the hydroxyl group at the 5'-end of the nucleic acid is labeled with $^{33}$P.

Figure 2:
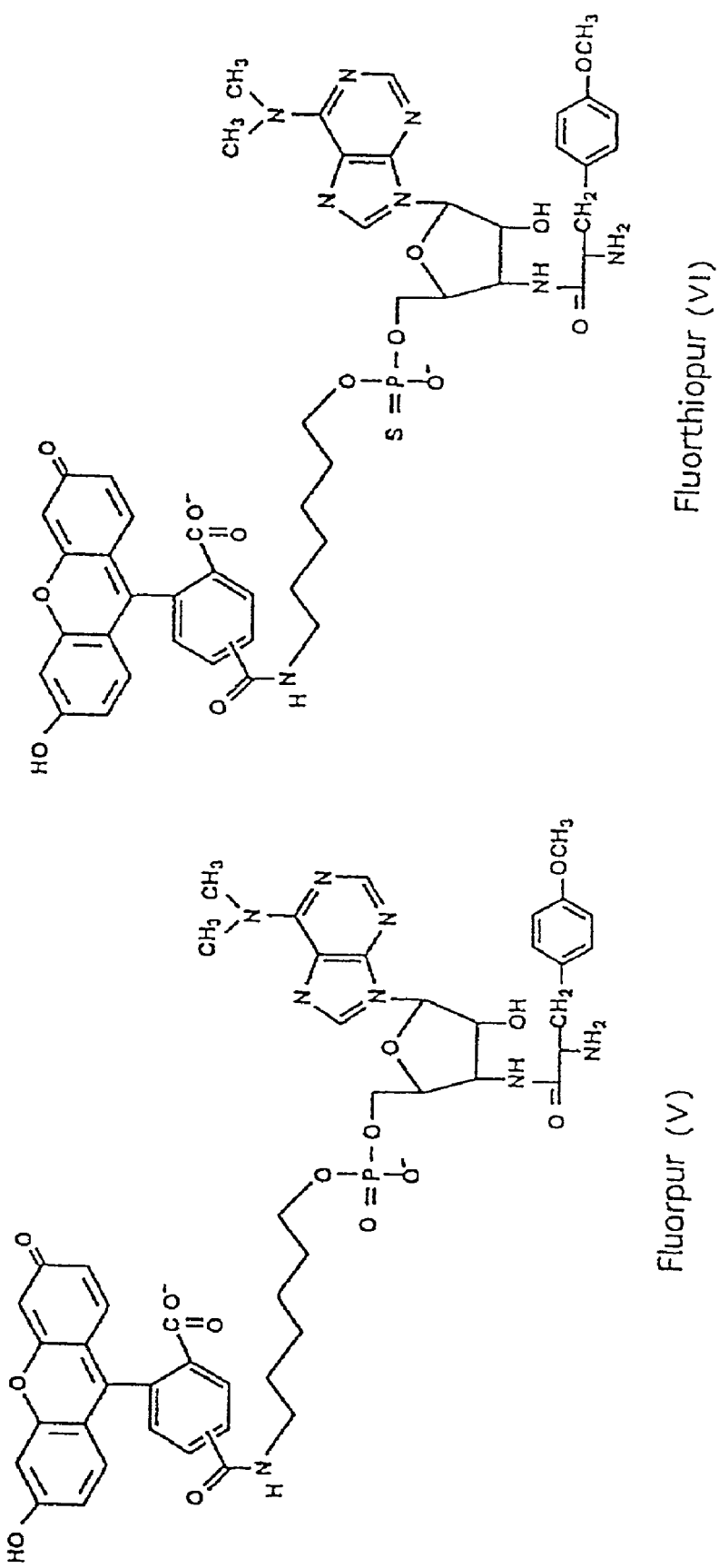
FIG. 2 shows the chemical structure of puromycin bound to a fluorescent substance. V is Fluorpur and VI is Fluorthiopur.

Also, fluorescent labeling compounds, for example, Fluorpur (Compound V in FIG. 2) and Fluorthiopur (Compound VI in FIG. 2), in which a fluorescent dye, for example, fluorescein, as the label portion and a compound comprising a nucleic acid bound to an amino acid or a compound having a chemical structure skeleton resembling an amino acid, for example, puromycin as the acceptor portion are linked to each other through a chemical bond, can be obtained by coupling puromycin and fluoredite and then removing the protective group.

The protein to which the labeling compound is added at the C-terminal thereof is not limited to a particular one.

The protein to which the labeling compound is added at the C-terminal thereof can be produced by the production method of the present invention described hereinbelow.

The production method for the above-described protein according to the present invention comprises the step of carrying out synthesis of a protein in a cell-free protein synthesis system or in a living cell in the presence of a labeling compound comprising a label portion comprising a label substance and an acceptor portion comprising a compound having an ability of binding to a C-terminal of a synthesized protein when protein synthesis is carried out in the cell-free protein synthesis system or in the living cell, the labeling compound being present at a concentration effective for the labeling compound to bind to the C-terminal of the synthesized protein.

As described above, the compound that constitutes the acceptor portion of the labeling compound has an ability of binding to a C-terminal of a synthesized protein when protein synthesis is carried out in a cell-free protein synthesis system or in a living cell so that the labeling compound could inhibit the protein synthesis depending on its concentration.

For example, puromycin (Compound I in FIG. 1) is known to inhibit the protein synthesis of bacteria (Nathans, D. (1964) Proc. Natl. Acad. Sci. USA, 51, 585–592; Takeda, Y. et al. (1960) J. Biochem., 48, 169–177) and animal cells (Ferguson, J. J. (1962) Biochim. Biophys. Acta, 57, 616–617; Nemeth, A. M. & de la Haba, G. L. (1962) J. Biol. Chem., 237, 1190–1193). The chemical structure of puromycin resembles that of aminoacyl tRNA and reacts with peptidyl tRNA that is bound to the P-site of ribosome and liberated from the ribosome as peptidyl puromycin, resulting in termination of the protein synthesis (Harris, R. J. (1971) Biochim. Biophys. Acta, 240, 244–262).

However, in the present invention, the protein synthesis is carried out in the presence of the labeling compound at a concentration effective for the labeling compound to bind to the C-terminal of the synthesized protein, that is, at a concentration where the protein synthesis in a cell-free protein synthesis system or in a living cell is not inhibited and where it can be linked in an amount allowing detection to the C-terminal of the protein, thereby linking the labeling compound to the C-terminal of the protein.

Though not desiring to be bound to any theory, the reason why the labeling compound is linked to the C-terminal of the synthesized protein would presumably be that in protein synthesis in the presence of the labeling compound at a low concentration such that the protein synthesis is not inhibited, when a termination codon comes to the A-site of a ribosome, the labeling compound is linked to the C-terminal of protein by the action of peptidyltransferase in competition with the termination factor.

The concentration which is effective for the labeling compound to bind to the C-terminal of the synthesized protein can be determined by the method described in the examples below with respect to an actually used system.

Figure 3:
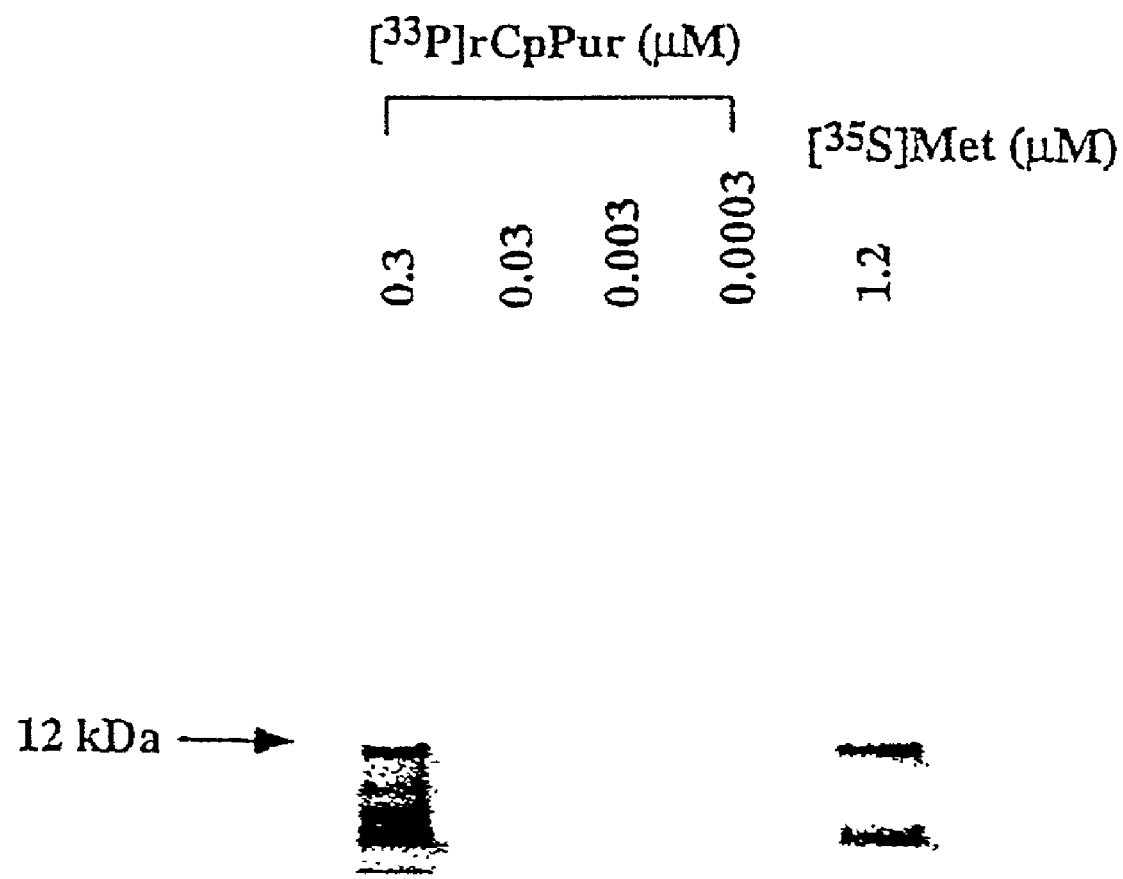
FIG. 3 is a photograph of electrophoretogram illustrating binding of $^{33}$P-rCpPur to the C-terminal of thioredoxin. Labeling was performed by reaction in a cell-free transcription-translation system of *Escherichia coli* in the presence of 0.0003, 0.003, 0.03, or 0.3 μM of $^{33}$P-rCpPur at 37° C. for 30 minutes. The rightmost lane indicates labeling of thioredoxin under the same conditions except for using $^{35}$S-methionine.

For example, examination of labeling of the translated protein labeled with the above-described labeling compound in the presence of a plasmid containing a promoter and coding regions for various proteins, for example, T7 promoter and a coding region for thioredoxin in a cell-free transcription-translation system of *E. coli*, shows the concentration range (0.1 to 1 µM) where $^{33}$P-rCpPur is evidently linked to the C-terminal of the full-length protein of thioredoxin (apparent molecular weight: 12 kDa) (FIG. 3). The radiolabeling of the full-length protein of thioredoxin with $^{33}$P-rCpPur or the like can be confirmed in a cell-free transcription-translation system containing nuclease treated rabbit reticulocyte lysate or wheat germ lysate. Similarly confirmed optimal concentrations of Fluorpur and Fluorthiopur necessary for radiolabeling are 0.3 to 50 µM in the system containing nuclease treated rabbit reticulocyte lysate and 10 to 50 µM in the case of the system containing wheat germ lysate.

If the label portion is replaced by various substances, evaluation can be made similarly. Also, fluorescent labeling compounds, for example, Fluorpur (Compound V in FIG. 2) and Fluorthiopur (Compound VI in FIG. 2), in which a fluorescent dye, for example, fluorescein, as the label portion and an amino acid or a compound having a chemical structure skeleton resembling amino acid, for example, puromycin, as the acceptor portion are linked to each other through a chemical bond can be evaluated as follows.

Figure 4:
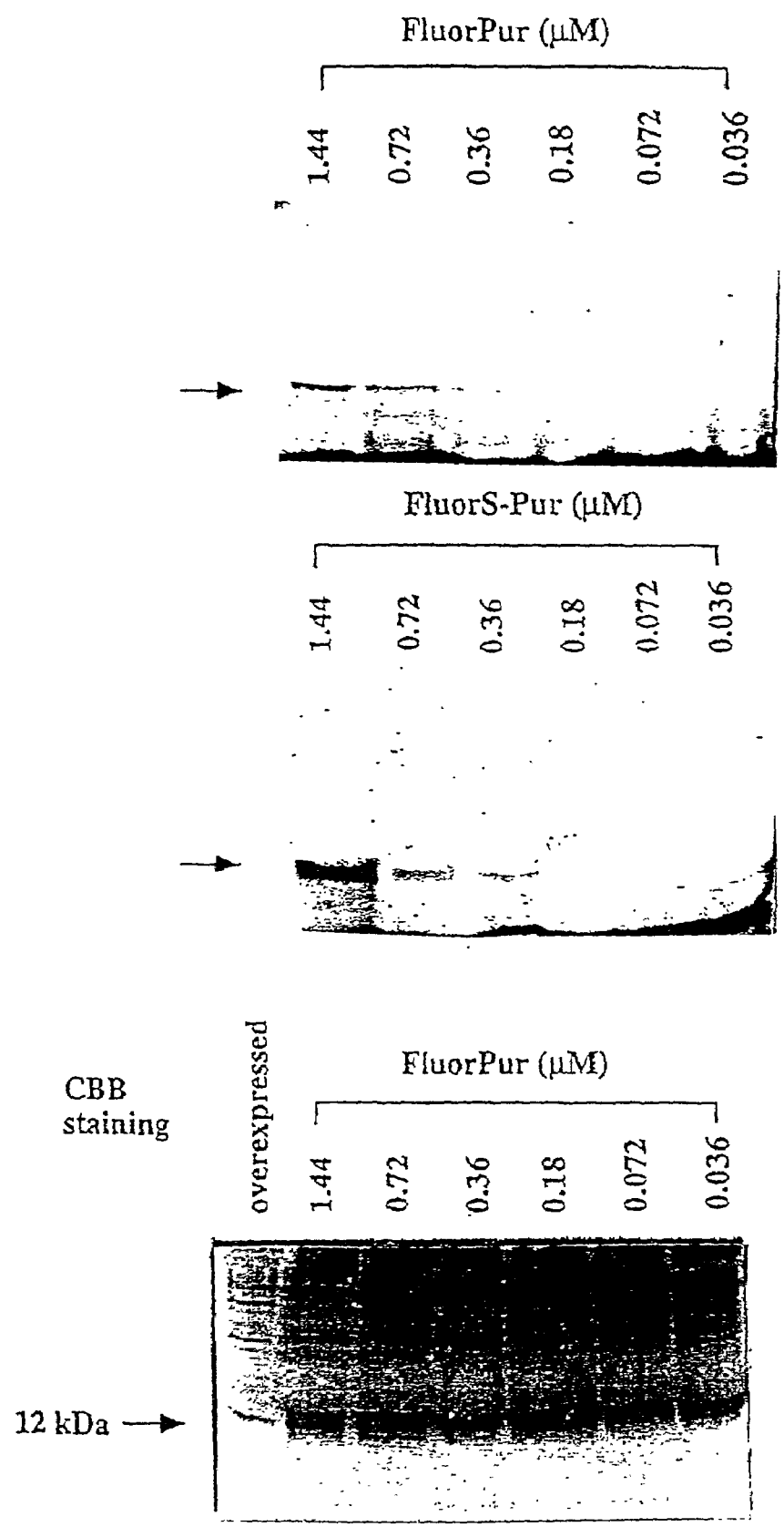
FIGS. 4A, 4B and 4C are photographs of electrophoretogram illustrating binding of puromycin bound to a fluorescent substance to the C-terminal of thioredoxin. Labeling was performed by reaction in a cell-free transcription-translation system of *Escherichia coli* in the presence of 0.036, 0.072, 0.18, 0.36, 0.72, or 1.44 μM of Fluorpur or Fluorthiopur at 37° C. for 30 minutes. The FIG. 4A electrophoretogram indicates the influence of Fluorpur (Fluor-Pur) concentration

Examination of fluorescent labeling of the translated protein labeled with the above-described fluorescent labeling compound in the presence of a plasmid containing a promoter and coding regions for various proteins, for example, T7 promoter and a coding region for thioredoxin in a cell-free transcription-translation system of *E. coli*, shows the concentration range (0.3 to 1.5 µM) where Fluorpur or Fluorthiopur is evidently linked to the C-terminal of the full-length protein of thioredoxin (apparent molecular weight: 12 kDa) (FIG. 4). The fluorescent labeling of the full-length protein of thioredoxin with Fluorpur and Fluorthiopur can be confirmed also in a cell-free transcription-translation system containing nuclease treated rabbit reticulocyte lysate or wheat germ lysate. Similarly confirmed optimal concentrations of Fluorpur and Fluorthiopur necessary for fluorescent labeling are 0.3 to 50 µM in the system containing nuclease treated rabbit reticulocyte lysate and 10 to 50 µM in the case of the system containing wheat germ lysate.

The present invention further provides a method for analyzing a function of a gene, comprising the steps of: adding a nucleic acid containing the gene to a cell-free protein synthesis system as a template; carrying out protein synthesis in the presence of the labeling compound to obtain a protein having the labeling compound attached to the C-terminal of the protein, the labeling compound being present at a concentration effective for the labeling compound to bind to the C-terminal of the synthesized protein; and analyzing a function of the labeled protein.

The analysis method of the present invention utilizes the method for producing a labeled protein according to the present invention. More specifically, it is the same as the method for producing the labeled protein except for the steps of adding a nucleic acid containing a gene to a cell-free protein synthesis system as a template and analyzing a function of the labeled protein.

As the gene for analyzing its function may be used those accumulated by genome analysis.

The nucleic acid containing a gene may be any of genomic DNA, cDNA, and a transcription product of a gene. When DNA is used as the template, the cell-free protein synthesis system used is a cell-free transcription-translation system. In the case of the transcription product, either a cell-free transcription-translation system or a cell-free translation system may be used.

The function analysis of a protein may be selected properly depending on the object to be analyzed and preferably includes determination of a protein-protein interaction, determination of a protein-nucleic acid interaction, or determination of an interaction between a protein and a ligand capable of specifically binding to the protein.

The function of a gene can be analyzed by the analysis of the function of a protein.

Unless otherwise indicated, gene manipulating techniques such as construction of plasmids, translation in a cell-free protein synthesis system or the like can be operated by the method described in Samrook et al. (1989) Molecular Cloning, 2nd Edition, Cold Spring Harbor Laboratory Press or a method similar thereto.

According to the present invention, it is possible to label the C-terminal of a protein synthesized by translation using a cell-free protein synthesis system or a living cell regardless of whether it is from a procaryote or an eucaryote and therefore, the identification and function analysis of a protein expressed by the gene can be practiced rapidly, accurately, and economically.

EXAMPLES

Hereafter, the present invention will be described more concretely by examples. However, the following examples are construed as being an aid for obtaining concrete knowledge of the present invention but in no way limit the scope of the present invention.

Example 1

Preparation of a Labeling Compound and Labeling of a Protein Using the Compound

<1> Preparation of Labeling Compound
(a) Synthesis of rCpPur (ribocytidyl(3'→5')puromycin (II))
Material: Puromycin (3'-[α-amino-p-methoxyhydro-cinnamamido]-3'-deoxy-N,N'-dimethyladenosine, I) was purchased from Sigma; rC-β-amidite (N$^4$-benzoyl-5'-O-(4,4'-dimethoxytrityl)-2'-O-tert-butyldimethylsilyl)-cytidine-3'-O-[O-(2-cyanoethyl)-N,N'-diisopropylphosphoramidite]), dC-β-amidite (N$^4$-benzoyl-5'-O-(4,4'-dimethoxytrityl)-2'-O-deoxycytidine-3'-O-[O-(2-cyanoethyl)-N,N'-diisopropylphosphoramidite]), and dU-β-amidite (5'-O-(4,4'-dimethoxytrityl)-2'-deoxyuridine- 3'-O-[O-(2-cyanoethyl)-N,N'-diisopropylphosphoramidite]) were each purchased from Nippon Perceptive; tetrazole was purchased from Nippon Millipore; fluorinated tetrabutylammonium was purchased from Aldrich; QAE-Sephadex was purchased from Pharmacia; and silica gel for chromatography was purchased from Merck.

Method: Puromycin (50 mg, 92 μmol) was dissolved in 2 ml of dry pyridine, evaporated under reduced pressure and dehydrated. This procedure was repeated 3 times. To this were added 15 ml of 4% tetrazole/acetonitrile solution and rC-β-amidite, and the mixture was stirred at room temperature. The reaction was monitored by silica gel thin layer chromatography (TLC, developing solvent: chloroform:methanol=9:1). Usually, the reaction was completed in 1 day. After the reaction was over, the solvent was removed under reduced pressure, and 3 ml of a solution of 0.1 M iodine in tetrahydrofuran/pyridine/water=80:40:2 was added thereto. The resulting phosphite triester was oxidized while stirring at room temperature. After 1 hour and half, the solvent was removed under reduced pressure and the residue was extracted with chloroform. After the extract was dried over anhydrous magnesium sulfate, the solvent was removed under reduced pressure. This was applied to silica gel column chromatography and eluted with chloroform/methanol=90:10. Ribocytidyl puromycin (CpPur) with a protective group was eluted at Rf 0.32 on the silica gel TLC (development solvent: chloroform:methanol=9:1). Then, the protective groups were removed. Ribocytidylpuromycin with a protective group was treated initially with 0.5 ml of aqueous 80% acetic acid solution at room temperature for 1 hour to effect detritylation. After removing acetic acid under reduced pressure, 0.5 ml of a mixed solution of concentrated aqueous ammonia/ethanol=2:1 was added to remove a β-cyanoethyl group and a benzoyl group. After allowing to stand at room temperature for 15 hours, the solvent was removed under reduced pressure, and to the residue was added 0.5 ml of 1 M tetrabutylammonium fluoride in tetrahydrofuran to deprotect the t-butyldimethylsilyl group attached to the 2'—OH group. After 30 minutes, the solvent was removed under reduced pressure and the residue was applied to QAE-Sephadex column chromatography and eluted with a linear gradient of 0 to 0.5 M triethylamine carbonate. The eluted solutions were collected and lyophilized. Thus, 10 mg of ribocytidylpuromycin was obtained. The synthetic product was identified as ribocytidylpuromycin because nuclease P1 digestion gave the same amounts of cytidine and puromycin 5'-phosphoric acid and a molecular ion of [M+H]$^+$ appears at m/z 777 in MALDI/TOF mass spectrometry. dCpPur (deoxycytidyl(3'→5')puromycin (III) and dUpPur (deoxyuridyl(3'→5')puromycin (IV) were synthesized and identified, respectively, in the same manner as the above-described rCpPur from dc-β-amidite (N$^4$-benzoyl-5'-O-4,4'-dimethoxytrityl)-2'-deoxycytidine-3'-O-[O-(2-cyanoethyl)-N,N'-diisopropylphosphoramidite]) and dU-β-amidite (5'-O-4,4'-dimethoxytrityl)-2'-deoxyuridine-3'-O-[O-(2-cyanoethyl)-N,N'-diisopropylphosphoramidite]) and puromycin as starting materials.

(b) Preparation of fluoresceinylphosphopuromycin (Fluorpur, V) and fluoresceinylthiophophopuromycin (Fluorthiopur, VI) Material: Puromycin was purchased from Sigma, fluoredite (6-N-carboxy-di-O-pivaloyl-fluoresceinhexyl-O-(2-cyanoethyl)-(N,N'-diisopropyl)-phosphoramidite) was purchased from Nippon Perceptive, tetrazole was purchased from Nippon Millipore, TETD (tetraethylthiuram disulfide) was purchased from ABI, and silica gel for chromatography was purchased from Merck.

Method: Puromycin (26 mg, 48 μmol) was dissolved in 3 ml of dry pyridine, evaporated under reduced pressure and dehydrated. This procedure was repeated 3 times. To this were added 5 ml of 4% tetrazole/acetonitrile solution and fluoredite, and the mixture was stirred at room temperature. The reaction was monitored by silica gel thin layer chromatography (TLC, developing solvent: chloroform:methanol=9:1). Usually, the reaction was completed in 2 hours. After the reaction was over, the solvent was removed under reduced pressure and 2 ml of a solution of 0.1 M iodine in tetrahydrofuran/pyridine/water=80:40:2 was added thereto. The resulting phosphite triester was oxidized while stirring at room temperature. After 1 hour and half, the solvent was removed under reduced pressure and the residue was extracted with chloroform. After the extract was dried over anhydrous magnesium sulfate, the solvent was removed under reduced pressure. This was applied to silica gel column chromatography and eluted with chloroform/methanol=90:10. Fluorpur with a protective group was eluted at Rf 0.26 on the silica gel TLC (development solvent: chloroform:methanol=9:1). Then, the protective groups were removed. Fluorpur with a protective group was added to 1 ml of a mixed solution of concentrated aqueous ammonia/ethanol=2:1 to remove a β-cyanoethyl group, thus giving 7 mg of Fluorpur (V). The synthetic product was identified as Fluorpur (V) because ultraviolet and visible rays absorption spectra of its solution at pH 9 appear at 272 nm (attributed to puromycin moiety) and 494 nm (attributed to fluorescein moiety) and a molecular ion of [M+H]$^+$ appears at m/z 1010 in MALDI/TOF mass spectrometry. Fluorthiopur was synthesized in the same manner as Fluorpur except that after the coupling of puromycin and fluoredite, 1 ml of acetonitrile solution of TETD was added instead of iodine and stirred at room temperature for 30 minutes to sulfurate the phosphite triester. After the reaction was over, the solvent was removed under reduced pressure and the residue was extracted with chloroform. The extract was dried over anhydrous magnesium sulfate and the solvent was removed under reduced pressure. This was applied to silica gel chromatography and eluted with chloroform/methanol=90:10. Fluorthiopur with a protective group was eluted at Rf 0.33 on the silica gel TLC (development solvent: chloroform:methanol=9:1). Then, the protective groups were removed. Fluorthiopur with a protective group was added to 1 ml of a mixed solution of concentrated aqueous ammonia/ethanol=2:1 to remove a β-cyanoethyl group, thus giving 6 mg of Fluorthiopur (VI). The synthetic product was identified as Fluorthiopur (VI) because ultraviolet and visible rays absorption spectra of its solution at pH 9 appear at 272 nm (attributed to puromycin moiety) and 494 nm (attributed to fluorescein moiety) and a molecular ion of [M+H]$^+$ appears at m/z 1026 in MALDI/TOF mass spectrometry.

<2> Preparation of Plasmid

The plasmid (pT-Trx) containing T7 promoter and a coding region for thioredoxin (135 amino acid residues, molecular weight: 14 kDa, apparent molecular weight: 12 kDa) of *E. coli* were donated by Mr. Shunsuke Ishii of the Institute of Physical and Chemical Research. The host was *E. coli* strain BL21(DE3). The *E. coli* strain BL21(DE3) harboring the plasmid (pT-Trx) was incubated in LB medium in the presence of chloramphenicol (final concentration 34 μg/ml) at 37° C. for 10 hours and the cells were collected by centrifugation. Plasmid DNA was purified by cesium chloride density gradient centrifugation (Nozawa and Ebihara, Recombinant DNA Experiment Note—Basic Operations, pp. 63–67, Gendai-Kogakusha, 1991).

<3> Method for Labeling Protein (a) Labeling of Protein Using rCpPur rCpPur (30 pmol) was phosphorylated by T4 polynucleotide kinase (10 units) in the presence of γ-$^{33}$P-ATP (9.25 MBq). The reaction was carried out under the condition of 37° C. for 1 hour. After the reaction was over, the reaction mixture was heated at 70° C. for 20 minutes to inactivate the enzyme.

Labeling reaction was carried out using a cell-free transcription-translation system of *E. coli*. The reaction mixture (25 μl) of the cell-free transcription-translation system of *E. coli* had the following composition: 7.5 μl of *E. coli* S30 extract (containing T7 RNA polymerase), 10 μl of *E. coli* S30 premix, 2.5 μl of an amino acid mixed solution, 1 μl of an RNase inhibitor, 1 μg of plasmid (thioredoxin), and 0.0003 to 0.3 μM (final concentration) of the $^{33}$P-rCpPur described above. As a control, the reaction was carried out also in a system containing $^{35}$S-methionine (1.2 μM). After the reaction was carried out at 37° C. for 30 minutes, precipitation was performed with acetone. A buffer solution (pH 8) containing 1% SDS was added to the precipitate, and then heated at 90° C. for 5 minutes for dissolution, separated by SDS-15% polyacrylamide gel electrophoresis, and analyzed using an image analyzer (Fuji Photo Film, BAS 2000). FIG. 3 shows the results of examination of labeling of thioredoxin with $^{33}$P-rCpPur. When the concentration of $^{33}$P-rCpPur was 0.3 μM, a distinct band corresponding to the full-length thioredoxin was detected at the position of apparent molecular weight of 12 kDa. The result shows that $^{33}$P-rCpPur is linked to the C-terminal of thioredoxin. The band with an apparent molecular weight of 12 kDa was detected even when labeled with $^{35}$S-methionine (final concentration: 1.2 μM) (FIG. 3). In a similar manner, it was confirmed that $^{33}$P-dCpPur and $^{33}$P-dUpPur were linked to the C-terminal of thioredoxin.

(b) Fluorescent Labeling of a Protein With Fluorpur and Fluorthiopur

Fluorescent labeling of a protein by a cell-free transcription-translation system of *E. coli* in the presence of Fluorpur and Fluorthiopur was examined. The reaction mixture (25 μl) of the cell-free transcription-translation system of *E. coli* had the following composition: 7.5 μl of *E. coli* S30 extract (containing T7 RNA polymerase), 10 μl of *E. coli* S30 premix, 2.5 μl of an amino acid mixed solution, 1 μl of an RNase inhibitor, 1 μg of plasmid (thioredoxin), and Fluorpur (final concentration: 0.036 to 1.44 μM) or Fluorthiopur (final concentration: 0.036 to 1.44 μM). After the reaction was carried out at 37° C. for 30 minutes, precipitation was performed with acetone. A buffer solution (pH 8) containing 1% SDS was added to the precipitate, then heated at 90° C. for 5 minutes for dissolution, separated by SDS-15% polyacrylamide gel electrophoresis, and detected for fluorescent bands of protein using a fluorescent gel scanner (Fluor Imager 585, Molecular Dynamics). Measurement was made at an excitation wavelength of 488 nm and an emission wavelength of 520 nm. FIGS. 4A, 4B and 4C show the results of fluorescent labeling of thioredoxin with Fluorpur and Fluorthiopur. For both Fluorpur and Fluorthiopur in a concentration ranges of 0.36 to 1.44 μM, fluorescent bands were detected at the position of apparent molecular weight of 12 kDa indicated by an arrow (FIGS. 4A and 4B). The results show that Fluorpur and Fluorthiopur are linked to the C-terminal of the full-length protein (apparent molecular weight: 12 kDa) (cf. the band of mass expressed thioredoxin in FIG. 4C) of thioredoxin. Also, it revealed that Fluorthiopur was incorporated more or less efficiently as compared with Fluorpur.

The fluorescent labeling of the full-length protein of thioredoxin with Fluorpur and Fluorthiopur was confirmed also in a cell-free transcription-translation system containing nuclease treated rabbit reticulocyte lysate or wheat germ lysate. The respective optimal concentrations of Fluorpur and Fluorthiopur necessary for fluorescent labeling were 0.3 to 50 µM in the system containing nuclease treated rabbit reticulocyte lysate and 10 to 50 µM in the case of the system containing wheat germ lysate.

What is claimed is:

1. A method for analyzing a function of a protein, comprising the steps of:
    i) producing a labeled protein which consists of a protein portion and a labeling compound chemically linked to a C-terminal of the protein portion by the steps of adding a nucleic acid containing a gene to a cell-free protein synthesis system as a template, and performing protein synthesis in the presence of the labeling compound to produce the labeled protein consisting of the protein portion and the labeling compound chemically linked to the C-terminal of the protein portion, wherein the labeling compound consists of a) an acceptor portion and b) a non-radioactive label substance chemically linked to the acceptor portion, wherein said acceptor portion comprises one member selected from the group consisting of puromycin, a puromycin derivative having the ability to bind to the C-terminal of a synthesized protein when protein synthesis is performed in a cell-free protein synthesis system or in a living cell, 3'-N-aminoacylpuromycin aminonucleoside and 3'-N-aminoacyladenine aminonucleoside, wherein said labeling compound is present at a concentration effective for said labeling compound to bind to the C-terminal of the synthesized protein, said protein being translated in the presence of said labeling compound;
    ii) contacting the labeled protein with a target molecule; and
    iii) determining an interaction between the labeled protein and the target molecule, to thereby analyze a function of the labeled protein.

2. The method according to claim 1, wherein said acceptor portion comprises puromycin.

3. The method according to claim 1, wherein said acceptor portion comprises a puromycin derivative.

4. The method according to claim 3, wherein said puromycin derivative is one member selected from the group consisting of ribocytidyl puromycin, deoxycytidyl puromycin and deoxyuridyl puromycin.

5. The method according to claim 1, wherein said non-radioactive label substance is a fluorescent dye.

6. The method according to claim 5, wherein said fluorescent dye is fluorescein.

7. The method according to claim 1, wherein said labeling compound is fluoresceinylphosphopuromycin or fluoresceinylthiophosphopuromycin.

* * * * *